United States Patent
Qiu

(10) Patent No.: US 11,259,568 B2
(45) Date of Patent: Mar. 1, 2022

(54) LIQUID STORAGE ASSEMBLY, ATOMIZER AND ELECTRONIC CIGARETTE HAVING THE SAME

(71) Applicant: Joyetech Europe Holding GmbH, Zug (CH)

(72) Inventor: Weihua Qiu, Jiangsu (CN)

(73) Assignee: JOYETECH EUROPE HOLDING GMBH, Zug (CH)

( * ) Notice: Subject to any disclaimer, the term of this patent is extended or adjusted under 35 U.S.C. 154(b) by 243 days.

(21) Appl. No.: 16/466,024

(22) PCT Filed: May 9, 2017

(86) PCT No.: PCT/CN2017/083558
§ 371 (c)(1),
(2) Date: Jun. 1, 2019

(87) PCT Pub. No.: WO2018/098996
PCT Pub. Date: Jun. 7, 2018

(65) Prior Publication Data
US 2020/0069894 A1 Mar. 5, 2020

(30) Foreign Application Priority Data
Dec. 2, 2016 (CN) .......................... 201611101684.X

(51) Int. Cl.
*A24F 40/42* (2020.01)
*A24F 40/49* (2020.01)
*A24F 40/10* (2020.01)
*A61M 11/04* (2006.01)
*A61M 15/00* (2006.01)

(52) U.S. Cl.
CPC .............. *A24F 40/42* (2020.01); *A24F 40/49* (2020.01); *A61M 11/042* (2014.02); *A61M 15/0001* (2014.02); *A24F 40/10* (2020.01)

(58) Field of Classification Search
CPC ...... A24F 47/00; A24F 47/008; A24F 47/004; A24F 40/42; A24F 40/49; A24F 40/10; A61M 15/001
See application file for complete search history.

(56) References Cited

U.S. PATENT DOCUMENTS 9,894,932 B2 * 2/2018 Liu ........................ G01N 21/84
9,894,937 B2 * 2/2018 Li ............................ H05B 3/14
2014/0182612 A1 7/2014 Chen
(Continued)

FOREIGN PATENT DOCUMENTS

CN 104939320 A 9/2015
CN 204907926 U 12/2015
(Continued)

*Primary Examiner* — Alex B Efta
(74) *Attorney, Agent, or Firm* — Novick, Kim & Lee, PLLC; Allen Xue

(57) ABSTRACT

A liquid storage assembly includes a liquid storage tube having a liquid storage chamber, a sealing member, an adjusting member, and a lower cover. The sealing member is received in the liquid storage tube and defines a second liquid intake hole fluidly communicating with the liquid storage chamber. The adjusting member is received in the liquid storage tube and is rotatable relative to the sealing member, the adjusting defines a communicating portion corresponding to the second liquid intake hole.

10 Claims, 16 Drawing Sheets

(56) References Cited

U.S. PATENT DOCUMENTS

| | | |
|---|---|---|
| 2015/0245661 A1 | 9/2015 | Milin |
| 2016/0219934 A1* | 8/2016 | Li ............................ B65D 85/70 |
| 2017/0281883 A1* | 10/2017 | Li .......................... A61M 11/041 |
| 2018/0035718 A1* | 2/2018 | Liu ........................ A61M 11/042 |

FOREIGN PATENT DOCUMENTS

| | | |
|---|---|---|
| CN | 105686088 A | 6/2016 |
| CN | 205432130 U | 8/2016 |
| CN | 106136328 A | 11/2016 |
| WO | 2015013953 A1 | 2/2015 |

* cited by examiner

LIQUID STORAGE ASSEMBLY, ATOMIZER AND ELECTRONIC CIGARETTE HAVING THE SAME

FIELD OF TECHNOLOGY

The invention relates to a technical field of smoking simulation, and more particularly, relates to a liquid storage assembly, an atomizer, and an electronic cigarette.

BACKGROUND

Related electronic cigarette generally has a split type structure, the liquid storage assembly and the atomizing assembly is connected to each other by a pluggable structure or a simple threaded structure. When the liquid storage assembly is detached and separated from the atomizing assembly, the tobacco liquid inlet/outlet of the liquid storage assembly remains open, thus the tobacco liquid stored in the liquid storage assembly can be leaked out easily. When such kind of electronic cigarette is accessible for children, the liquid storage assembly and the atomizing assembly may be detached from each other merely by simple operation such as plugging or rotation, thus children may contact or swallow the tobacco liquid by an accident, it has a potential safety hazard for children's health.

SUMMARY

Accordingly, it is necessary to provide a liquid storage assembly having a children protective function, an atomizer having the liquid storage assembly, and an electronic cigarette, a contact or swallowing of the tobacco liquid by children can be effectively avoided, when the electronic cigarette opened by children.

The technical solution adopted by the present disclosure to solve the problem is that:

A liquid storage assembly, includes a liquid storage tube having a liquid storage chamber, a sealing member, an adjusting member, and a lower cover. The sealing member is received in the liquid storage tube and defines a second liquid intake hole fluidly communicating with the liquid storage chamber. The adjusting member is received in the liquid storage tube and is rotatable relative to the sealing member, the adjusting defines a communicating portion corresponding to the second liquid intake hole. The lower cover is positioned on an end of the liquid storage tube. Wherein the lower cover or the sealing member is provided with a blocking portion, the adjusting member is provided with an resisting portion capable of resisting the blocking portion, when the liquid storage assembly is disassembled, the adjusting member is rotated to enable the resisting portion to reach and resist the blocking portion, causing the adjusting member to seal the second liquid storage chamber to close the liquid storage chamber.

Further, an internal wall of the lower cover is provided with a restriction portion, a number of the blocking portion is two, the two blocking members are opposite to each other and are protruded from the restricting portion, the resisting portion is capable of resisting the restricting portion along an axial direction and resisting the blocking portion along a circumferential direction.

Further, the liquid storage tube is provided with an exhaust tube therein, the exhaust tube is arranged along an axial direction of the liquid storage tube and extends through the liquid storage tube, the liquid storage chamber is constituted by an space between an internal wall of the liquid storage tube and an external wall of the exhaust tube.

Further, the liquid storage assembly further includes a pressing member received in the liquid storage tube, the pressing member defines a first liquid intake hole corresponding to the second liquid intake hole, the first liquid intake hole is fluidly communicating with the liquid storage chamber, the sealing member is provided with at least one positioning protrusion, the pressing member defines a positioning hole corresponding to the at least one positioning protrusion, the pressing member is fixedly connected to the sealing member via an engagement between the at least one position protrusion and the positioning hole.

Further, the liquid storage assembly further includes an auxiliary adjusting member fixed to the adjusting member and positioned between the adjusting member and the sealing member, the auxiliary adjusting member defines an auxiliary communicating portion corresponding to the communicating portion, an end of the auxiliary adjusting member away from the adjusting member roatatably resists the sealing member, the communicating portion is capable of fluidly communicating with the second liquid intake hole via the auxiliary communicating portion.

Further, the adjusting member is provided with at least one first protrusion, the auxiliary adjusting member defines a first latching groove corresponding to the at least one first protrusion, the adjusting member is fixedly connected to the auxiliary adjusting member via an engagement between the at least one first protrusion and the first latching groove.

Further, the exhaust tube is provided with at least one second protrusion at an end adjacent to the atomizing assembly, the at least one second protrusion protrudes along an axial direction of the exhaust tube, the sealing member defines a second latching groove corresponding to the at least one second protrusion, the sealing member is fixedly connected to a liquid storage carrier via an engagement between the at least one second protrusion and the second latching groove.

Further, the sealing member and the auxiliary adjusting member are made of ceramic materials.

Further, an internal wall of the lower cover is provided with a restriction portion, a number of the blocking portion is two, the two blocking members are opposite to each other and are protruded along an axial direction of the sealing member from a lower end of the sealing member, the resisting portion is capable of resisting the restricting portion along an axial direction and resisting the blocking portion along a circumferential direction.

An atomizer includes an aforementioned liquid storage assembly and an atomizing assembly detachably connected to the liquid storage assembly.

An electronic cigarette includes an aforementioned atomizer and a battery pack connected to the liquid storage assembly.

The advantages of the present disclosure are described as follows:

In the electronic cigarette provided by the present disclosure, the close of the liquid storage chamber is controlled by a rotation of the adjusting member, when children open the electronic cigarette, the adjusting member is rotated to disconnect the communicating portion from the second liquid intake hole, and the liquid storage chamber is closed. A leakage of the tobacco liquid is avoided, a contact or swallowing of the tobacco liquid by children can be effectively avoided, it has a simple structure and can be easily operated.

BRIEF DESCRIPTION OF THE DRAWINGS

The invention is specifically illustrated with reference to accompanying drawings and embodiments in the following description.

Figure 1:
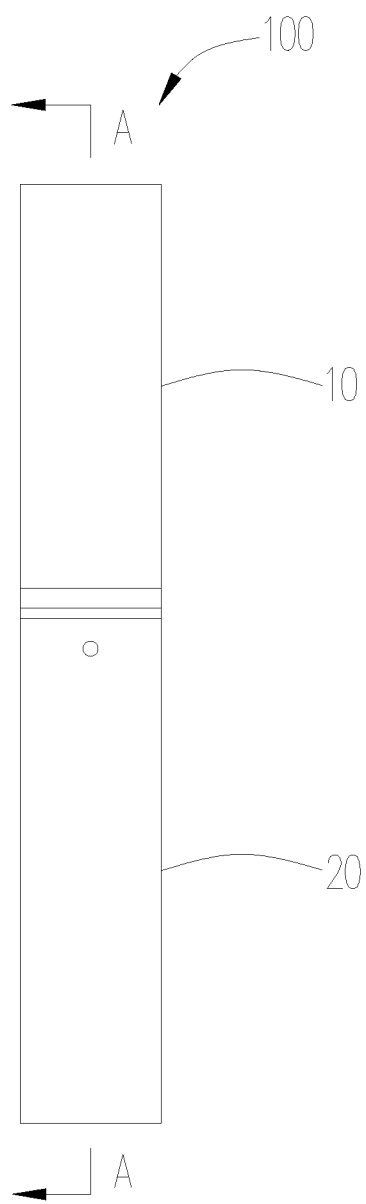
FIG. 1 is a structural view of an electronic cigarette of a first embodiment of the preset disclosure.

Designations and reference numerals of the part and component in the accompanying drawings.

| | | |
|---|---|---|
| electronic cigarette 100 | liquid storage assembly 10 | atomizing assembly 20 |
| liquid storage carrier 11 | pressing member 12 | sealing member 13 |
| adjusting member 14 | lower cover 15 | auxiliary adjusting member 16 |
| housing 21 | battery 22 | atomizing base 23 |
| heating mechanism 24 | atomizing end cover 25 | liquid storage tube 112 |
| exhaust tube 113 | liquid storage chamber 114 | exhaust passage 115 |
| first mounting hole 121 | first liquid intake hole 122 | positioning hole 123 |
| main body 131 | connecting body 132 | third mounting hole 141 |
| communicating portion 142 | sealing portion 143 | resisting portion 144 |
| internal thread 145 | first protrusion 146 | first latching protrusion 151 |
| restricting portion 152 | blocking portion 153 | auxiliary communicating portion 161 |
| auxiliary mounting hole 162 | first latching groove 163 | air intake hole 211 |
| supporting base 231 | electrode fixing bracket 232 | absorbing member 241 |
| heating member 242 | second latching member 251 | fourth mounting hole 252 |
| third liquid intake hole 253 | external thread 254 | resisting portion 1121 |
| second protrusion 1131 | second mounting hole 1311 | second liquid intake hole 1312 |
| positioning protrusion 1313 | first restricting groove 1314 | second latching groove 1315 |
| air intake groove 2311 | through hole 2312 | elongated groove 2313 |
| second restricting groove 2314 | auxiliary sealing portion 164 | pressure sensor 26 |
| atomizing chamber 255 | electronic cigarette 200 | |
| electronic cigarette 300 | liquid storage assembly 30 | atomizing assembly 40 |
| liquid storage tube 31 | connecting ring 32 | upper cover 33 |
| mouth piece 34 | lower cover 35 | sealing member 36 |
| adjusting member 37 | atomizing base 41 | atomizing end cover 42 |
| air regulating member 43 | atomizing head 44 | connecting portion 321 |
| annular groove 351 | restricting portion 352 | blocking portion 361 |
| exhaust passage 362 | second liquid intake hole 363 | resisting portion 371 |
| communicating portion 372 | internal thread 373 | first electrode 411 |
| external thread 421 | first internal thread 422 | second electrode 442 |
| resisting portion 431 | first external thread 441 | first sealing member 38 |
| through hole 4421 | liquid storage chamber 311 | |

DETAILED DESCRIPTION OF EMBODIMENTS

The invention is specifically illustrated with reference to accompanying drawings. The accompanying drawings are schematic views which simplified shows fundamental structures of an exemplary embodiment of the invention. Thus, merely the constructions related to the invention are shown.

The First Embodiment

Referring to FIG. 1, the present disclosure provides an electronic cigarette 100, the electronic cigarette 100 includes an atomizer (not labeled) and a battery pack connected to the atomizer. The atomizer includes a liquid storage assembly 10 configured for storing tobacco liquid, and an atomizing assembly 20 configured for atomizing the tobacco liquid to form aerosol, the liquid storage assembly 10 is detachably connected to the atomizing assembly 20. The battery assembly is detachably connected to the atomizing assembly 20.

Figure 2:
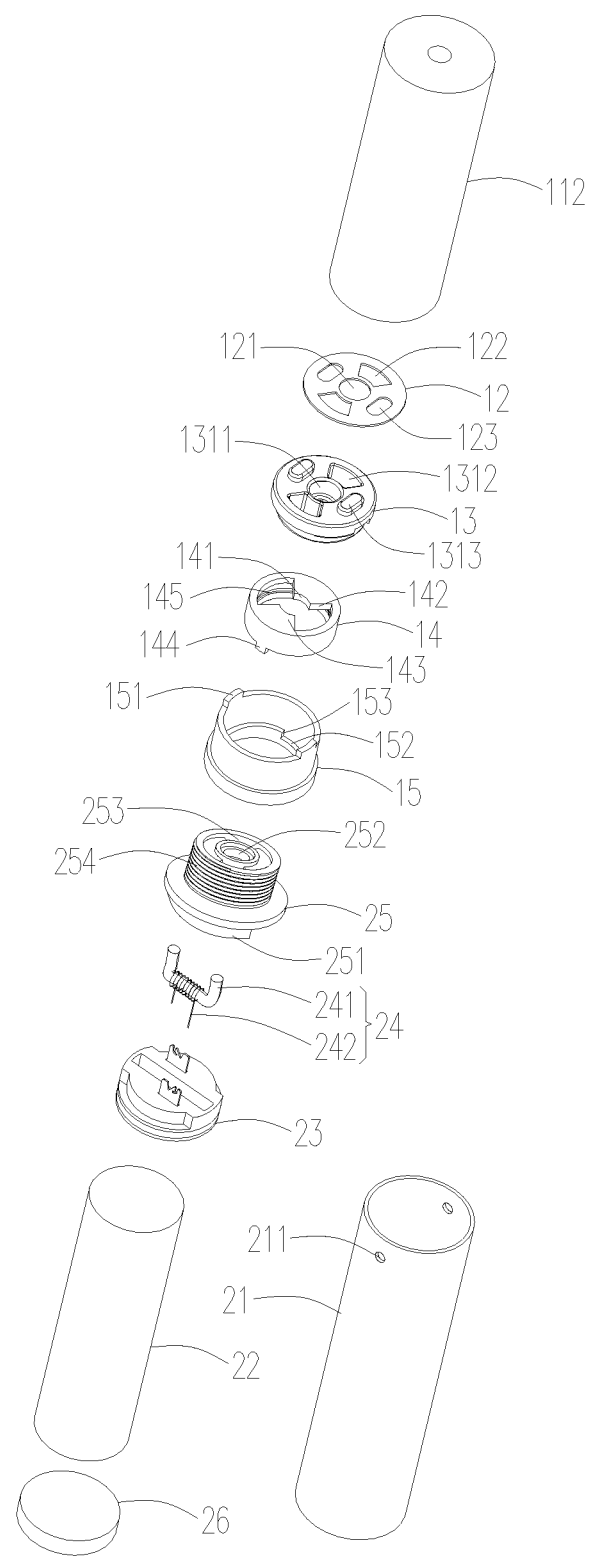
FIG. 2 is an exploded view of the electronic cigarette of FIG. 1.
Figure 3:
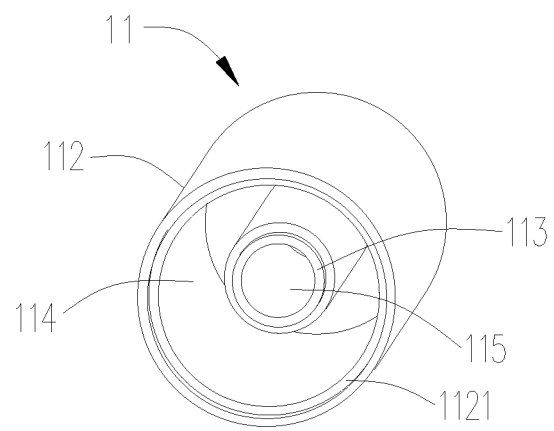
FIG. 3 is a structural view of a liquid storage carrier of the electronic cigarette of FIG. 2.

Also referring to FIG. 2 and FIG. 3, the liquid storage assembly 10 includes a liquid storage carrier 11, a pressing member 12, a sealing member 13 and an adjusting member 14, and a lower cover 15 detachably assembled to an end of the liquid storage carrier 11 adjacent to the atomizing assembly 20. The pressing member 12, the sealing member 13 and the adjusting member 14 are received in the liquid storage carrier 11. The adjusting member 14 is rotatably positioned between the sealing member 13 and the lower cover 15.

Further, the liquid storage carrier 11 substantially has a cylindrical shape. The liquid storage carrier 11 includes a liquid storage tube 112 having an opening at an end, and an exhaust tube 113 received in and extending through the liquid storage tube 112. The exhaust tube 113 is positioned on a center of the liquid storage tube 112. A liquid storage chamber 114 is formed between an internal wall of the liquid storage tube 112 and an external wall of the exhaust tube 113, the liquid storage chamber 114 is configured to store the tobacco liquid. The interior space of the exhaust tube 113 forms an exhaust passage 115 for user to inhale. User can smoke via a top of the exhaust tube 113.

Further, the liquid storage tube 112 forms a resisting portion 1121 having an annular shape and extending along a circumferential direction of the liquid storage tube 112. The resisting portion 1121 forms on the internal wall of the liquid storage tube 112 and is adjacent of the opening.

In the illustrated embodiment, the liquid storage carrier 11 can serve as a mouth-piece directly. User keeps an end of the liquid storage carrier 11 in his mouth and performs a smoke. It can be understood that, in alternative embodiment, a communicating member can be connected to the liquid storage carrier 11 for fluidly communicating with the exhaust tube 113, user keeps an end of the communicating member in his mouth and performs a smoke.

Referring to FIG. 2, the pressing member 12 substantially has a disc sheet structure. The pressing member 12 defines a first mounting hole 121 matching with the exhaust tube 113 at a center of the pressing member 12. The pressing member 12 defines a first liquid intake hole 122 and a positioning hole 123. The first liquid intake hole 122 and the positioning hole 123 surround the first mounting hole 121. The pressing member 12 is sleeved on the exhaust tube 113 via the first mounting hole 121 at the center. The edge of the pressing member 12 resists the resisting portion 1121 of the liquid storage tube 112, and is connected to the internal wall of the liquid storage tube 112 tightly.

In the illustrated embodiment, a number of the first liquid intake hole 122 is two, the two first liquid intake holes 122 are symmetrically arranged about the first mounting hole 121. A number of the positioning holes 123 is two, the two positioning holes 123 are symmetrically arranged about the first mounting hole 121. The first liquid intake holes 122 and the positioning holes 123 are uniformly distributed along a circle and are staggered arranged. It can be understood that, in alternative embodiment, the number of the first liquid intake hole 122 and the number of the positioning hole 123 can be one or more than two.

In the illustrated embodiment, the pressing member 12 is a plastic disc sheet. It can be understood that, in alternative embodiment, the pressing member 12 can be made of other hard materials such as stainless steel sheet or ceramic sheet.

Figure 4:
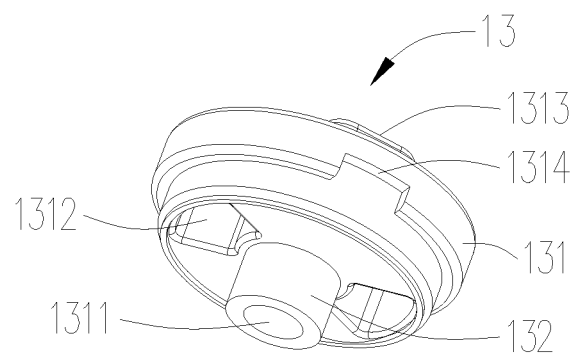
FIG. 4 is a structural view of a sealing member of the electronic cigarette of FIG. 2.

Also referring to FIG. 4, the sealing member 13 substantially has a cylinder shape. The sealing member 13 includes a main body 131 and a connecting body 132 protruded from a center of the main body 131. The connecting body 132 is positioned on an end of the main body 131 distal from the pressing member 12. The main body 131 defines a second mounting hole 1311 at the center, the second mounting hole 1311 extends through the connecting body 132 and matches the exhaust tube 113. The main body 131 defines a second liquid intake hole 1312 and forms a positioning protrusion 1313 corresponding to the positioning hole 123. The second liquid intake hole 1312 is corresponding to the first liquid intake hole 122 and surrounds the second mounting hole 1311. The main body 131 further defines a first restriction groove 1314 at a circumferential surface of the main body 131. The sealing member 13 is sleeved on an end of the exhaust tube 113 via the second mounting hole 1311. When the positioning protrusion 1313 matches and is connected to the positioning hole 123, the second liquid intake hole 1312 is fluidly communicated with the first liquid intake hole 122 of the pressing member 12. The sealing member 13 is tightly connected to the internal wall of the liquid storage tube 112. The second mounting hole 1311 is hermetically connected to the external wall of the exhaust tube 113.

In the illustrated embodiment, the sealing member 13 is made of rubber. It can be understood that, the sealing member 13 can also be made of silica gel, for providing a sealing function.

Due to a softness of the material of the sealing member 13, the pressing member 12 is configured to closely resist the sealing member 13 for improving a strength of the sealing member 13, enabling the sealing member 13 not to be deformed, thereby avoiding a liquid leakage.

In the illustrated embodiment, the restricting mode between the sealing member 13 and the pressing member 12 is realized by an engagement between the positioning protrusion 1313 and the positioning hole 123. It can be understood that, the pressing member 12 can be fixed to the sealing member 13 via adhering.

Figure 5:
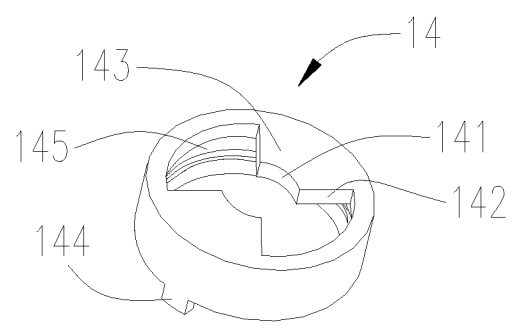
FIG. 5 is a structural view of an adjusting member of the electronic cigarette of FIG. 2.

Also referring to FIG. 5, the adjusting member 14 substantially has a sleeve shape, the adjusting member 14 defines a third mounting hole 141 corresponding to the connecting body 132 at a center of a bottom of the adjusting member 14. The adjusting member 14 defines a communicating portion 142 and is provided with a sealing portion 143 at a bottom of the adjusting member 14. The communicating portion 142 and the sealing portion 143 surround the third mounting hole 141. The adjusting member 14 is sleeved on the connecting body 132 of the sealing member 13 via the third mounting hole 141. When the adjusting member 14 is rotated, the communicating portion 142 and the sealing portion 143 can fluidly communicate with the second liquid intake hole 1312 of the sealing member 13 alternatively, thereby realizing an open or close of the second liquid intake hole 1312.

The adjusting member 14 is provided with an resisting portion 144, in the illustrated embodiment, the resisting portion 144 is a pair of protrusions opposite to each other. The pair of protrusions is protruded along an axial direction of the adjusting member 14 from an end of the adjusting member 14 adjacent to the atomizing assembly 20. The adjusting member 14 is provided with internal threads 145 at an internal wall of the adjusting member 14.

Figure 6:
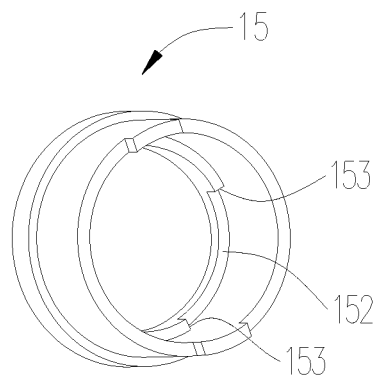
FIG. 6 is a structural view of a lower cover of the electronic cigarette of FIG. 2.

Referring to FIG. 2 and FIG. 6, the lower cover 15 is substantially a hollow cylindrical structure having two openings at opposite ends. The lower cover 15 is provided with a first latching protrusion 151 at an end away from the atomizing assembly 20, the first latching protrusion 151 matches with the first restricting groove 1314. The lower cover 15 is provided with a restricting portion 152 protruding inwardly from a circumferential surface of the lower cover 15, the restricting portion 152 is adjacent to the atomizing assembly 20. The restricting portion 152 has an annular shape, the restricting portion 152 is provided with a pair of blocking portions 153 protruding toward the adjusting member 14, the pair of blocking portions 153 is staggered from the resisting portion 144.

When the first latching protrusion 151 of the lower cover 15 is connected to and engages the first restricting groove 1314 of the sealing member 13, an end of the adjusting member 14 resists the sealing member 13 along an axially direction, an opposite end of the adjusting member 14 resists the restricting portion 152 along the axially direction. Thereby, an axial movement of the adjusting member 14 is restricted.

After the adjusting member 14 is rotated for an angle, the resisting portion 144 of the adjusting member 14 can resist the blocking portion 153 of the lower cover 15 along a circumferential direction, thereby restricting a rotation angle of the adjusting member 14.

Referring to FIG. 2, the atomizing assembly 20 includes a housing 21, an atomizing base 23 received in the housing 21, a heating mechanism 24 positioned on the atomizing base 23, and an atomizing end cover 25 detachably positioned on an end of the housing 21.

The battery pack (not labeled) includes a battery 22 received in the housing 21 and a control mechanism (not shown) controlling the battery 22 to direct power for the heating mechanism 24.

Further, the housing 21 substantially has a hollow tubular structure having an opening at an end of the housing 21. The tubular wall of the housing 21 defines two air intake holes 211 opposite to each other. The two air intake holes 211 are adjacent to the opening and are fluidly communicated with an interior of the housing 21. It can be understood that, a number of the air intake hole 211 can also be one or more than two.

Figure 7:
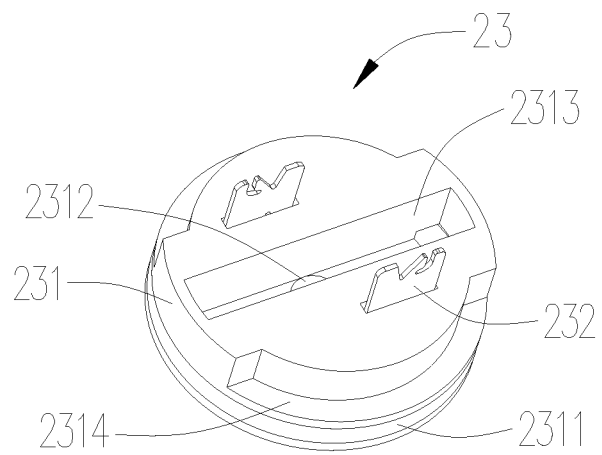
FIG. 7 is a structural view of an atomizing base of the electronic cigarette of FIG. 2.

Referring to FIG. 7, the atomizing base 23 has a disc structure, the atomizing base 23 includes a supporting base 231 closely received in the housing 21 and a pair of electrode fixing brackets 232 positioned on the supporting base 231.

The supporting base 231 defines an air intake groove 2311 surrounding a circumferential surface of the supporting base 231 and fluidly communicating with the air intake hole 211. The supporting base 231 defines a through hole 2312 at a lower end of the supporting base 231. The supporting base 231 defines a elongated groove 2313 at an upper end surface and fluidly communicating with the air intake groove 2311 and the through hole 2312. The supporting base 231 further defines a second restricting groove 2314 at a edge of the upper end surface of the supporting base 231.

The electrode fixing bracket 232 extends through the supporting base 231, the pair of electrode fixing brackets 232 are electrically connected to an anode and cathode of the battery 22, respectively.

Referring to FIG. 2, the heating mechanism 24 includes an absorbing member 241 and a heating member 242 electrically connected to the battery 22. The heating member 242 is wrapped up by the absorbing member 241 or the absorbing member 241 is wrapped up by the heating member 242. The absorbing member 241 is positioned on an upper end surface of the supporting base 231, the absorbing member 241 can be made of materials such as glass fiber or natural fiber which has a better tobacco liquid absorbing performance. Specifically, an end of the heating member 242 is connected to one of the electrode fixing bracket 232, an opposite end of the heating member 242 is connected to the other one electrode fixing bracket 232. The heating member 232 can be made of nichrome wire.

Figure 8:
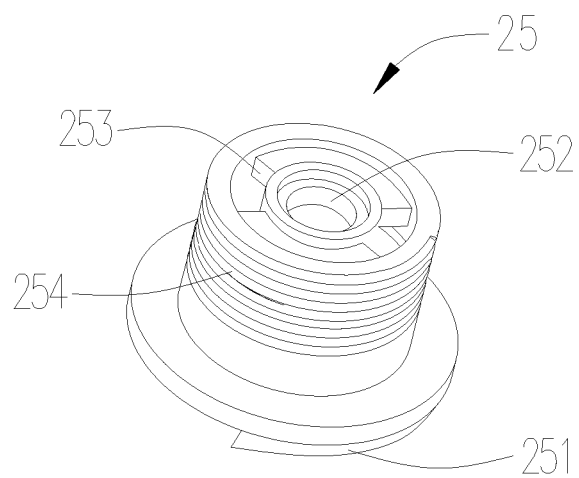
FIG. 8 is a structural view of an atomizing end cover of the electronic cigarette of FIG. 2.

Referring to FIG. 8, the atomizing end cover 25 substantially has a cylindrical structure having opposite ends fluidly communicating with each other and having a purfle. The atomizing end cover 25 is provided with a second latching protrusion 251 corresponding to the second restricting groove 2314, the second latching protrusion 251 is protruded from an end of the atomizing end cover 25 away from the liquid storage assembly 10 along an axial direction of the atomizing end cover 25. The atomizing end cover 25 defines a fourth mounting hole 252 at a center of a bottom of an end of the atomizing end cover 25 adjacent to the liquid storage assembly 10. The fourth mounting hole 252 is corresponding to the connecting body 132. The atomizing end cover 25 defines a third liquid intake hole 253 surrounding the fourth mounting hole 252. The external wall of the atomizing end cover 25 is provided with external threads 254 engaging with the internal threads 145 of the adjusting member 14.

Figure 9:
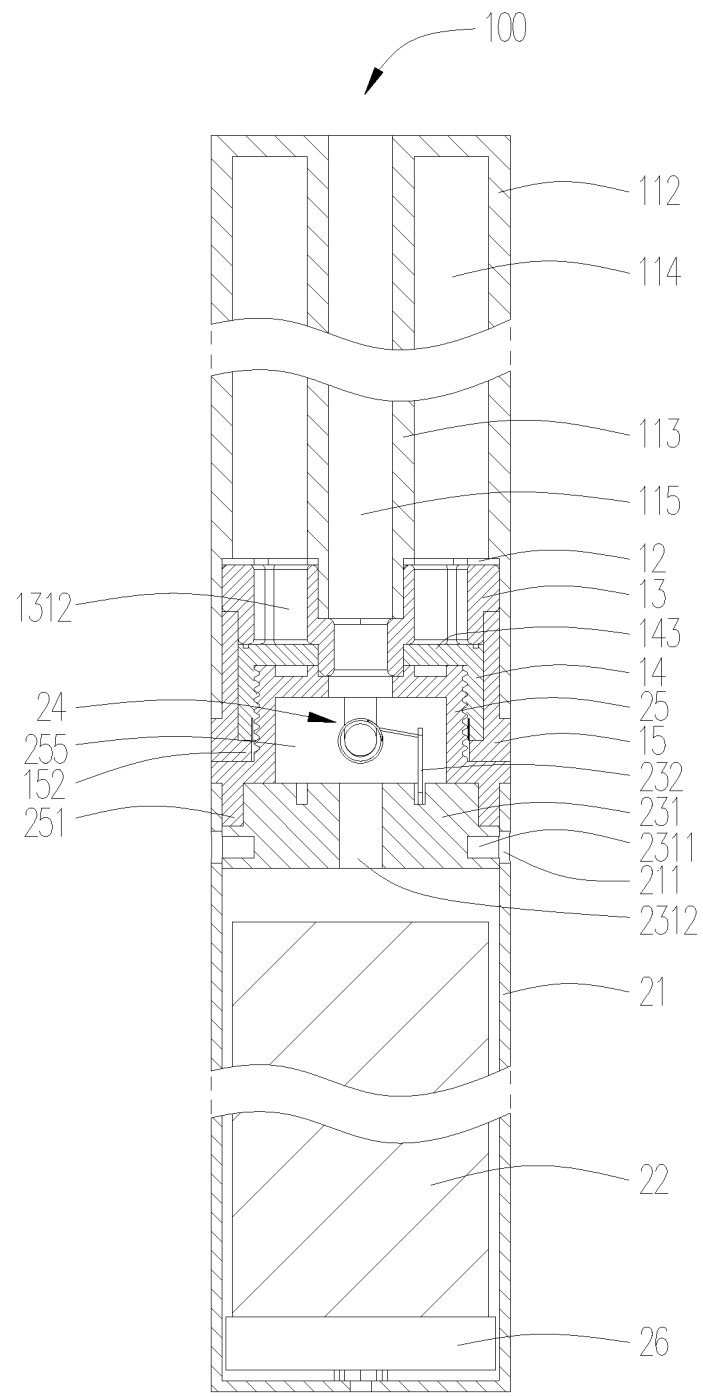
FIG. 9 is a cross-sectional view of the electronic cigarette of FIG. 1, take along ling A-A (showing a close state of the second liquid intake hole)

Also referring to FIG. 9, when assembly, the atomizing end cover 25 lathces with the atomizing base 23 via an engagement between the second latching protrusion 251 and the second restricting groove 2314. An atomizing chamber 255 is constituted by a space formed by the atomizing end cover 25 and the atomizing base 23, the heating mechanism 24 is received in the atomizing chamber 255.

In the illustrated embodiment, the control mechanism includes a pressure sensor 26 positioned in the interior of the housing 21, and a controller (not shown). An end of the controller is connected to the pressure sensor 26, an opposite end of the controller is connected to the battery. The pressure sensor 26 is fluidly communicated with the air intake hole 211. When user smoke, a negative pressure is generated in the housing 21. The pressure sensor 26 can detect a signal of a change of the pressure within the housing 21, and transfers the signal to the controller, thereafter, the controller controls the battery 22 to direct power for the heating member 241 of the heating mechanism 24, thereby an automatic powering on and heating can be realized.

It can be understood that, in alternative embodiment of the present disclosure, the control mechanism can also be a switch (not shown) mounted on the external wall of the housing 21, an end of the switch is connected to an electrode of the battery 22, an opposite end of the switch is connected to the fixing bracket 232. The switch can control the on/off state of the battery 22 and the heating mechanism 24. Specifically, the user takes one puff, the switch is required to be toggled one time, the battery 22 provides power of the heating mechanism 24 one time.

The operation procedure of the electronic cigarette 100 of the first embodiment of the present discourse is illustrated with reference to accompanying drawings as follow:

Referring to FIG. 9, at the initial state, the liquid storage assembly 10 of the electronic cigarette 100 is separated from the atomizing assembly 20, the resisting portion 144 of the adjusting member 14 resists one blocking portion 153 of the lower cover 15. The sealing portion 143 of the adjusting member 14 seals the second liquid intake hole 1312 of the sealing member 13, and the second liquid intake hole 1312 is closed. The tobacco liquid cannot flow out via the second liquid intake hole 1312 to be atomized.

Figure 10:
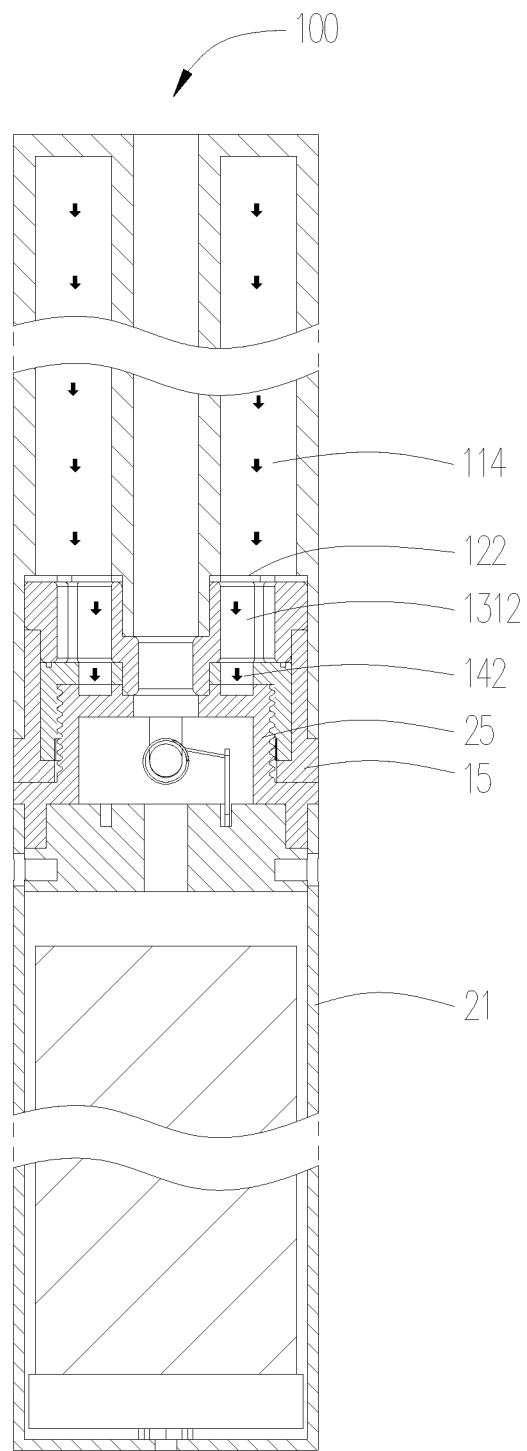
FIG. 10 is another cross-sectional view of the electronic cigarette (showing an open state of the second liquid intake hole)

Referring to FIG. 10, when use, the atomizing assembly 20 is rotated along a tightening direction, the internal threads 145 of the adjusting member 14 engages the external threads 254 of the atomizing end cover 25, when the screw force is greater than a friction force between the adjusting member 14 and the sealing member 13. The adjusting member 14 is then rotated together the atomizing end cover 25. When the resisting portion 144 is rotated to reach and resist the other blocking portion 153, the adjusting member 14 is then stopped. At the time, the communicating portion 142 of the adjusting member 14 is fluidly communicated with the second liquid intake hole 1312, the liquid storage chamber 114 is opened. The tobacco liquid flows into the atomizing chamber 255 by passing through the first liquid intake hole 122, the second liquid intake hole 1312, the communicating portion 142 and the third liquid intake hole 253 successively, and is then be absorbed by the absorbing member 241, the tobacco liquid is atomized by the heating member 242 to generate aerosol. The arrow in the FIG. 10 indicates a flowing direction of the tobacco liquid.

When the electronic cigarette 100 is required to enable the atomizing assembly 20 to separate from the liquid storage assembly 10, the atomizing assembly 20 is rotated along a loosened direction, when the screw force is greater than a friction force between the adjusting member 14 and the sealing member 13. The adjusting member 14 is then rotated together with the atomizing end cover 25, until the resisting portion 144 resists the other blocking portion 153, and the adjusting member 14 is stopped. The adjusting member 14 returns to the initial state as shown in FIG. 9, the sealing portion 143 seals the second liquid intake hole 1312, causing the liquid storage chamber 114 to be closed, the tobacco liquid is blocked, and cannot flow out.

When user inhales, air enters the electronic cigarette 100 via the air intake hole 211 of the housing 21, and enters the atomizing chamber 2515 of the atomizing end cover 25 via the air intake groove 2311 of the atomizing base 23 and the elongated groove 2313 successively. The mixed aerosol passes through the connecting body 132 of the sealing member 13 and finally enters user's mouth via the exhaust passage 115.

It can be understood that, the connecting body 132 can be omitted when the exhaust tube 113 is prolonged, enabling the exhaust tube 113 to extend through the pressing member 12, the sealing member 13, the adjusting member 14, and the atomizing end cover 25, causing the exhaust passage 115 to be directly fluidly communicated with the atomizing chamber 2515.

In the electronic cigarette 100 provided by the first embodiment of the present disclosure, when the liquid storage assembly 10 is detached and separated from the atomizing assembly 20, the adjusting member 14 is rotated to disconnect the communicating portion 142 from the second liquid intake hole 1312, and the liquid storage chamber 114 is closed. Even if children open it, a leakage of the tobacco liquid cannot occur, a contact or swallowing of the tobacco liquid by children can be effectively avoided, it has a better safety performance and a simple structure and it can be easily operated.

The Second Embodiment

The difference between the electronic cigarette 200 provided by the second embodiment of the present disclosure and the electronic cigarette 100 provided by the first embodiment is that, the liquid storage assembly 10 of the electronic cigarette 200 provided by the second embodiment has different structure, which is specifically illustrated in the following.

Figure 11:
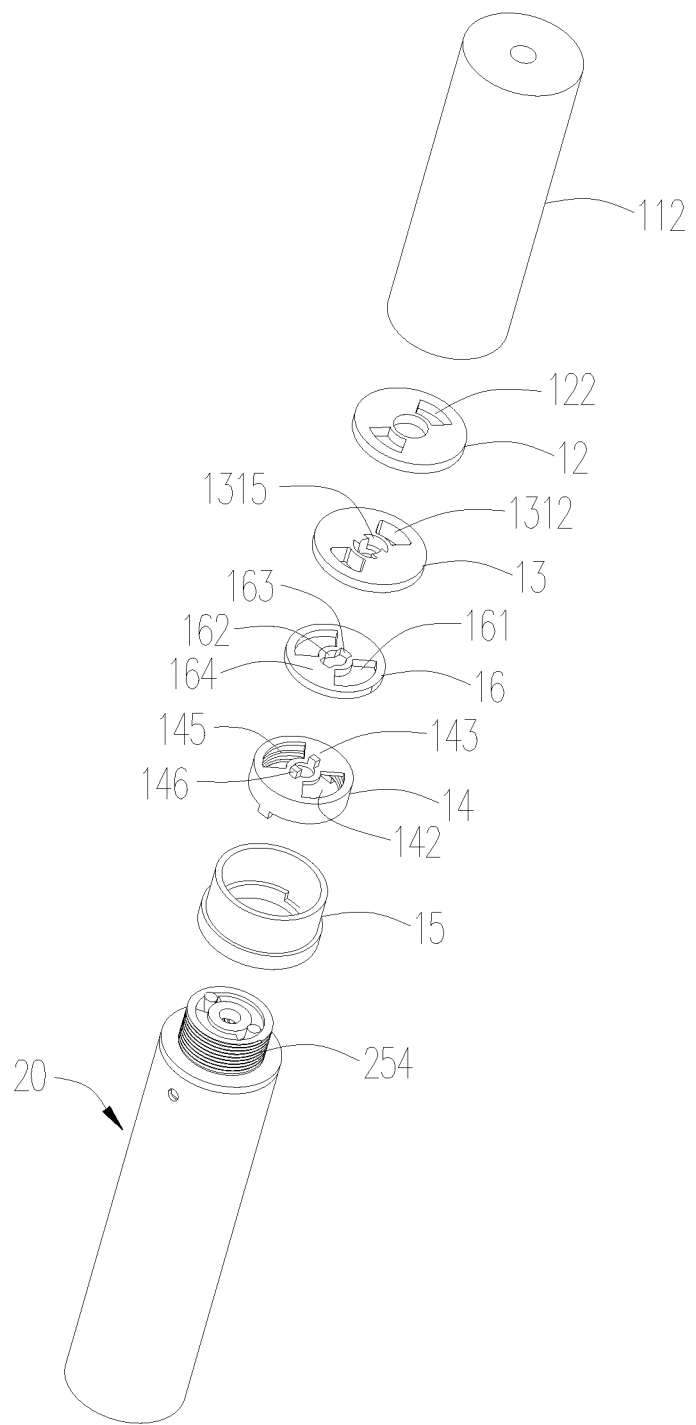
FIG. 11 is a partially exploded view of an electronic cigarette of a second embodiment of the present disclosure.

Referring to FIG. 11, the liquid storage assembly 10 includes a liquid storage carrier 11, a pressing member 12, a sealing member 13, an auxiliary adjusting member 16 and an adjusting member 14, and a lower cover 15 detachably assembled to an end of the liquid storage carrier 11 adjacent to the atomizing assembly 20. The liquid storage carrier 11, the pressing member 12, the sealing member 13, the auxiliary adjusting member 16 and the adjusting member 14 are received in the liquid storage carrier 11. The auxiliary adjusting member 16 is fixed to the adjusting member 14, the auxiliary adjusting member 16 is driven by the adjusting member 14 and is rotatably positioned between the sealing member 13 and the lower cover 15.

Figure 12:
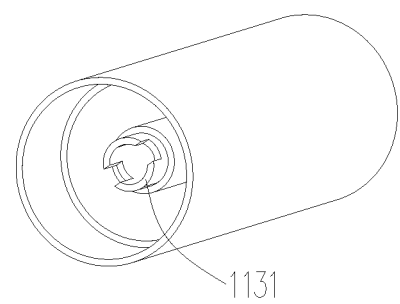
FIG. 12 is a structural view of a liquid storage carrier of the electronic cigarette of FIG. 11.

Also referring to FIG. 12, the liquid storage carrier 11 substantially has a tubular shape. The liquid storage carrier 11 includes a liquid storage tube 112 having an opening at an end and an exhaust tube 113 received in the liquid storage tube 112. The exhaust tube 113 extends through in the liquid storage tube 112 and is positioned on the center of the liquid storage tube 112. The exhaust tube 113 is provided with at least one second protrusion 1131 which is located at an end the exhaust tube 113 adjacent to the atomizing assembly 20 and protrudes along an axial direction of the exhaust tube 113.

The pressing member 12 substantially has a disc sheet structure. The pressing member 12 defines a first mounting hole 121 matching with the exhaust tube 113 at a center of the pressing member 12. The pressing member 12 defines a first liquid intake hole 122 surrounding the first mounting hole 121.

The sealing member 13 substantially has a disc sheet structure. The sealing member 13 defines a second mounting hole 1311 at a center corresponding to the exhaust tube 113. The sealing member 13 defines a second liquid intake hole 1312 corresponding to the first liquid intake hole 122 and surrounding the second mounting hole 1311, the sealing member 13 defines a second latching groove 1315 corresponding to the second protrusion 1131. When it is assembled, the second protrusion 1131 latches in the second latching groove 1315, enabling the sealing member 13 to fixedly connected to the exhaust tube 113.

The auxiliary adjusting member 16 substantially has a disc sheet structure. The auxiliary adjusting member 16 defines an auxiliary mounting hole 162 at a center corresponding to the exhaust tube 113. The auxiliary adjusting member 16 defines an auxiliary communicating portion 161 and is provided with an auxiliary sealing portion 164, the auxiliary communicating portion 161 and an auxiliary sealing portion 164 surround the auxiliary mounting hole 162. When the auxiliary adjusting member 16 is rotated, the auxiliary communicating portion 161 is enabled to be fluidly communicated with the second liquid intake hole 1312 or the auxiliary sealing portion 164 is enabled to seal the second liquid intake hole 1312.

Further, the auxiliary adjusting member 16 defines at least one first latching groove 163.

The adjusting member 14 substantially has a sleeve shape, the adjusting member 14 defines a third mounting hole 141 corresponding to the auxiliary mounting hole 162 at a center of a bottom of the adjusting member 14. The adjusting member 14 defines communicating portion 142 corresponding to the auxiliary communicating portion 161, the adjusting member 14 is provided with a sealing portion 143 corresponding to the auxiliary sealing portion 164. The adjusting member 14 is provided with an resisting portion 144. In the illustrated embodiment, the resisting portion 144 is a pair of protrusions opposite to each other. The pair of protrusions protrudes along an axial direction of the adjusting member 14 from an end of the adjusting member 14 and is adjacent to the atomizing assembly 20. The adjusting member 14 is provided with internal threads 145 at an internal wall of the adjusting member 14.

Further, the adjusting member 14 is provided with a first protrusion 146 corresponding to the first latching groove 163. In the illustrated embodiment, the first protrusion 146 latches within the first latching groove 163, for realizing a fixation between the adjusting member 14 and the auxiliary adjusting member 16. It can be understood that, the adjusting member 14 and the auxiliary adjusting member 16 can be fixedly connected via adhering.

The atomizing assembly 20 and the lower cover 15 of the liquid storage assembly 10 of the electronic cigarette 200 of the second embodiment have structures same as that in the first embodiment, which is not specifically described herein.

In illustrated embodiment, the sealing member 13 and the auxiliary adjusting member 16 are made of ceramic materials. Contact surfaces between the sealing member 13 and the auxiliary adjusting member 16 are smooth surfaces. When the auxiliary sealing portion 164 seals the second liquid intake hole 1312, a leakage of the tobacco liquid can be avoided. Further, the pressing member 12 closely resists an end surface of the sealing member 13 away from the adjusting member 14. The pressing member 12 can be made of rubber, and also can be made of silica gel. On one side, the external circumferential surface of the pressing member 12 closely contacts the internal circumferential surface of the liquid storage tube 112, providing a sealing function. On the other side, the ceramic material is fragile, when the pressure is greater, it can be crushed, therefore, the pressing member 12 can provide a buffing function, a destruction of the sealing member 13 and the auxiliary adjusting member 16 can be avoided.

Figure 13:
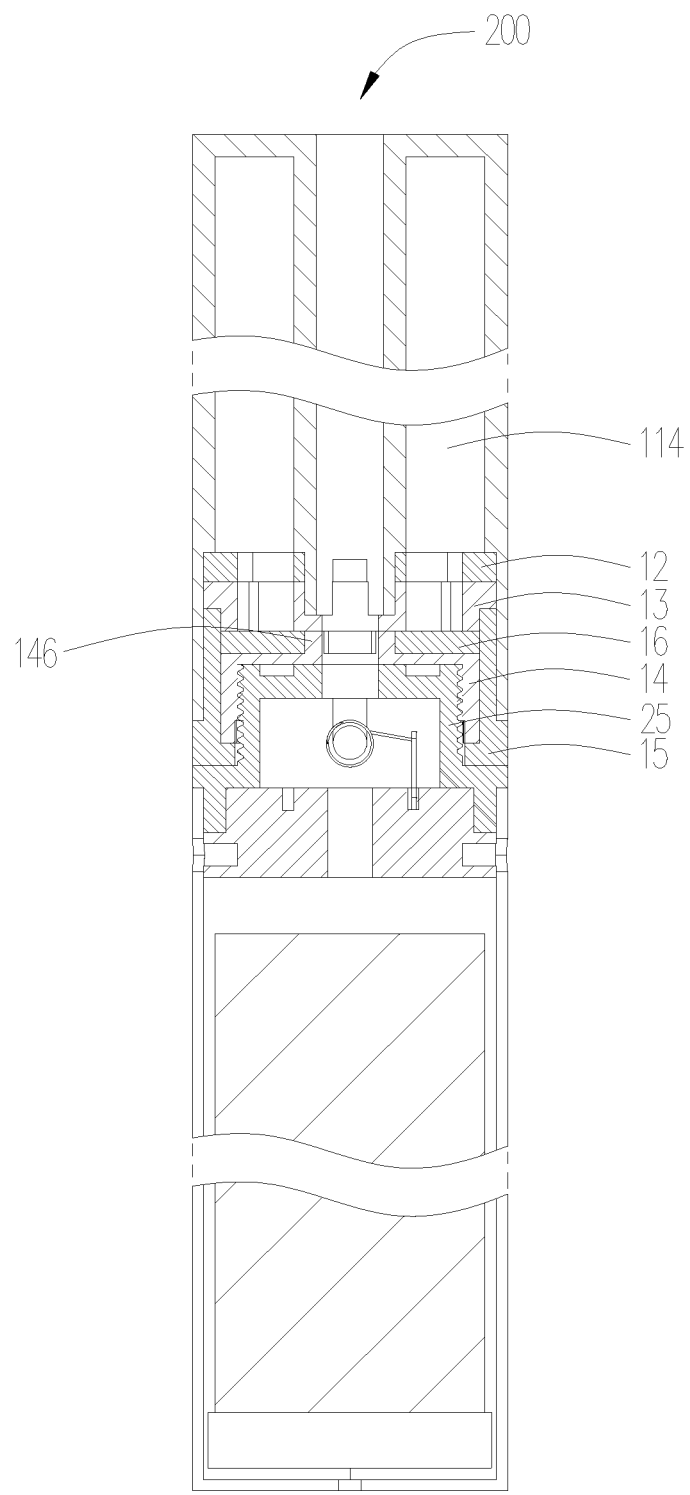
FIG. 13 is a cross-sectional view of the electronic cigarette of FIG. 12 (showing a close state of the liquid storage chamber)

The operation procedure of the electronic cigarette 200 of the second embodiment of the present discourse is illustrated with reference to accompanying drawings as follow:

Referring to FIG. 13, at an initial state, the liquid storage assembly 10 of the electronic cigarette 200 is separated from the atomizing assembly 20, the resisting portion 144 of the adjusting member 14 resists one blocking portion 153 of the lower cover 15. The auxiliary sealing portion 164 of the auxiliary adjusting member 16 seals the second liquid intake hole 1312 of the sealing member 13, and the second liquid intake hole 1312 is closed.

Figure 14:
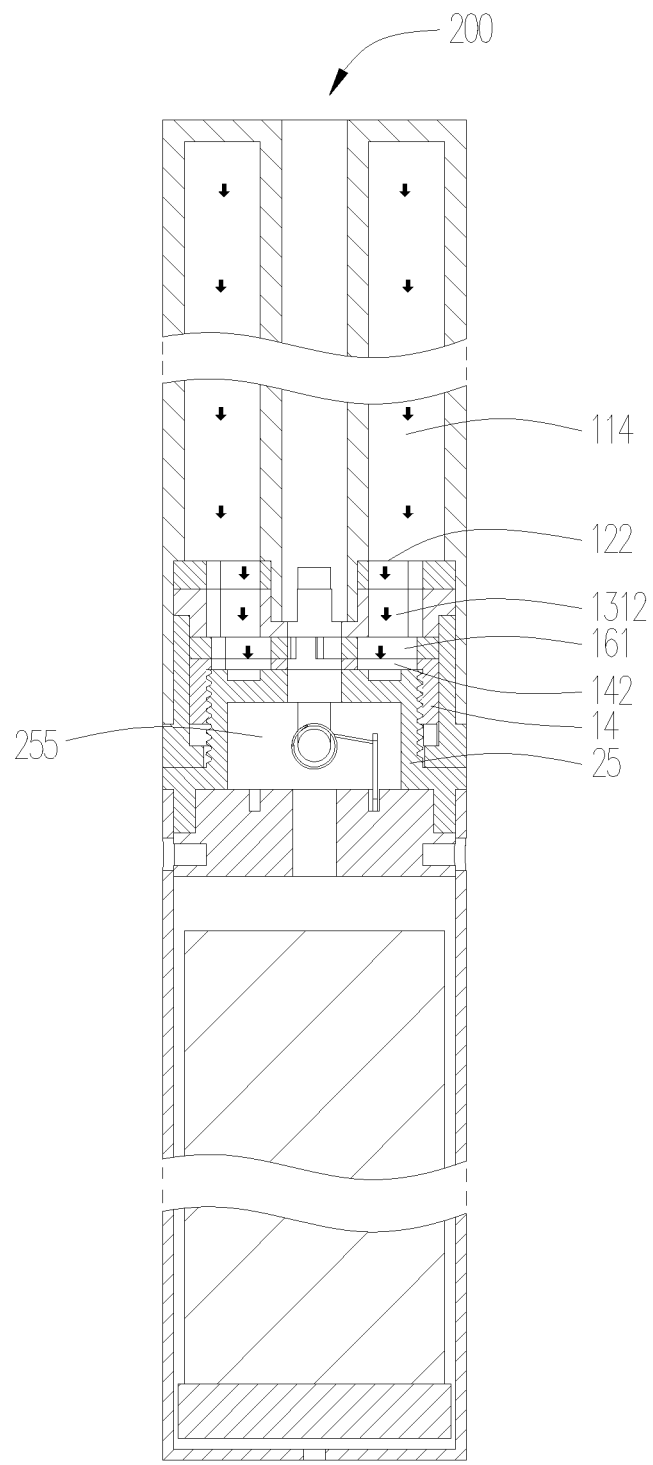
FIG. 14 is cross-sectional view of the electronic cigarette of FIG. 13 (showing an open state of the liquid storage chamber)

Referring to FIG. 14, when use, the atomizing assembly 20 is rotated along a tightening direction, the internal threads 145 of the adjusting member 14 engages the external threads 254 of the atomizing end cover 25. The auxiliary adjusting member 16 is driven by the adjusting member 14 to rotate together with the atomizing end cover 25. When the adjusting member 14 is rotated to enable the resisting portion 144 to resist the other one blocking portion 153, the auxiliary adjusting member 16 is then stopped. At the time, the auxiliary mounting portion 162 of the auxiliary adjusting member 16 is fluidly communicated with the second liquid intake hole 1312, the second liquid intake hole 1312 is opened. The tobacco liquid flows into the atomizing chamber 255 by passing through the first liquid intake hole 122, the second liquid intake hole 1312, the auxiliary communicating portion 142 and the third liquid intake hole 253 successively, and is then be absorbed by the absorbing member 241, the tobacco liquid is atomized by the heating member 242 to generate aerosol. The arrow in the FIG. 14 indicates a flowing direction of the tobacco liquid When the electronic cigarette 200 is disassembled to enable the atomizing assembly 20 to separate from the liquid storage assembly 10, the atomizing assembly 20 is rotated along a loosened direction. The adjusting member 14 is rotated together with the atomizing end cover 25, until the resisting portion 144 resists the blocking portion 153 and the adjusting member 14 is then stopped. The adjusting member 14 returns to the initial state as shown in FIG. 12, the auxiliary sealing portion 164 of the auxiliary adjusting member 16 seals the second liquid intake hole 1312 to block the tobacco liquid.

Compared the second embodiment to the first embodiment, a smooth contact is generated between the auxiliary adjusting member 16 and the sealing member 13, the friction force is less, the rotation of the adjusting member 14 is smooth, and the operation can be more convenient.

The Third Embodiment

Figure 15:
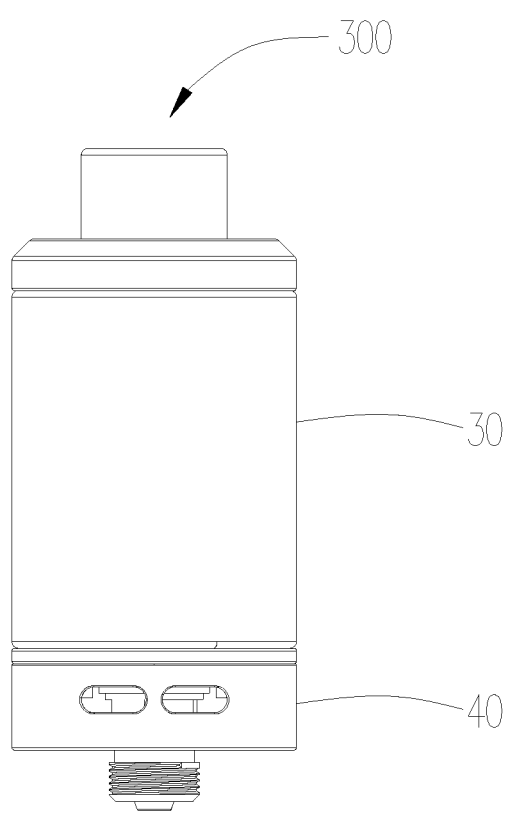
FIG. 15 is a structural view of an electronic cigarette of a third embodiment of the present disclosure.
Figure 16:
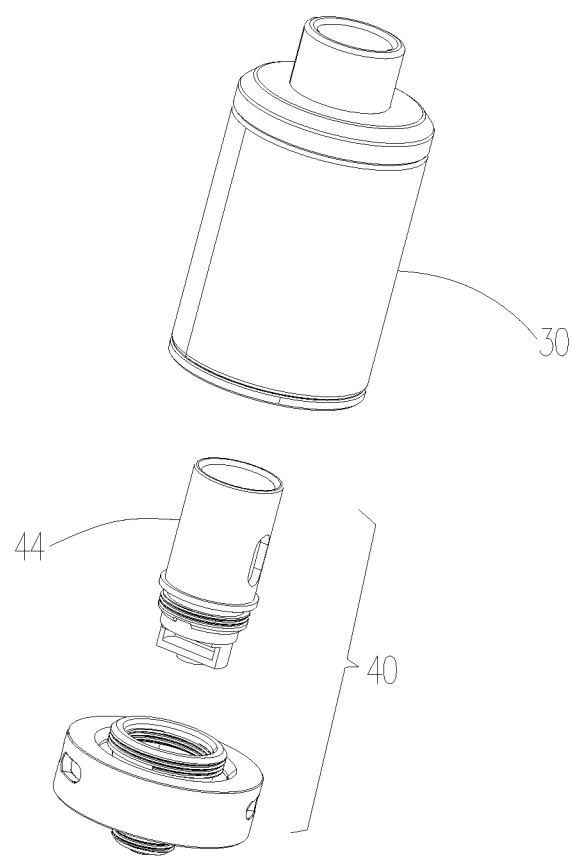
FIG. 16 is a partially exploded view of the electronic cigarette of FIG. 15.
Figure 17:
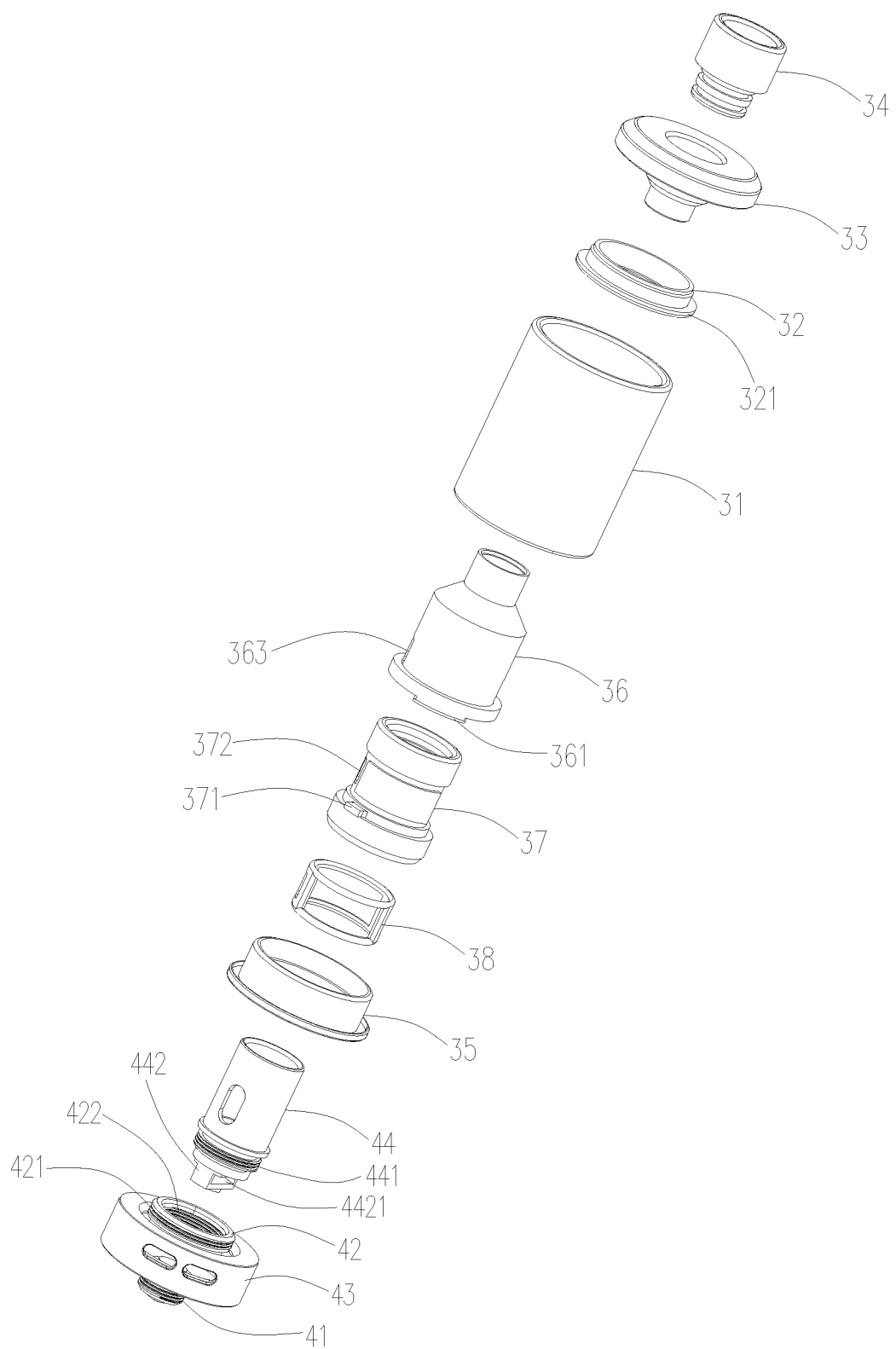
FIG. 17. is an exploded view of the electronic cigarette of FIG. 15.

Referring to FIG. 15 and FIG. 17, an electronic cigarette 300 is provided by the third embodiment. The electronic cigarette 300 includes an atomizer (not labeled) and a battery pack (not shown) detachably connected to the atomizer. The atomizer includes a liquid storage assembly 30 and an atomizing assembly 40 detachably connected to the lower end of the liquid storage assembly 30. The battery pack is mounted on the lower end of the atomizing assembly 40.

The liquid storage assembly 30 includes a liquid storage tube 31, a connecting ring 32 mounted on an upper end of the liquid storage tube 31, an upper cover 33 mounted on the connecting ring 32, a mouth piece 34 mounted on the upper cover 33, a lower cover 35 mounted on the lower end of the liquid storage tube 31, a sealing member 36 fixedly connected between the upper cover 33 and the lower cover 35, and an adjusting member 37 rotatably received in the sealing member 36.

The liquid storage tube 31 has a cylindrical structure, further, the liquid storage tube 31 is made of transparent material or translucent materials such as glass, facilitating for observing a residual amount of the tobacco liquid in the liquid storage tube 31.

The connecting ring 32 substantially has an annular structure, the external wall of the lower end of the connecting ring 32 is provided with a connecting portion 321 protruding along a radial direction of the connecting ring 32 from a circumferential surface of the connecting ring 32. The connecting portion 321 is connected to the upper end of the liquid storage tube 31 by an interference fit.

The upper cover 33 substantially has a circular dome structure with a cross-section having an inverted bow shape. The edge of the upper cover 33 is connected to an upper end of the connecting ring 32 by an interference fit.

The mouth piece 34 substantially has a tubular structure having two openings at opposite ends. The lower end of the mouth piece 34 is detachably connected to the center of the upper cover 33, and is fluidly communicated with the upper cover 33. It can be understood that, the mouth piece 34 can be detachably connected to the upper cover via latching, threaded connection or magnetic connection.

Figure 18:
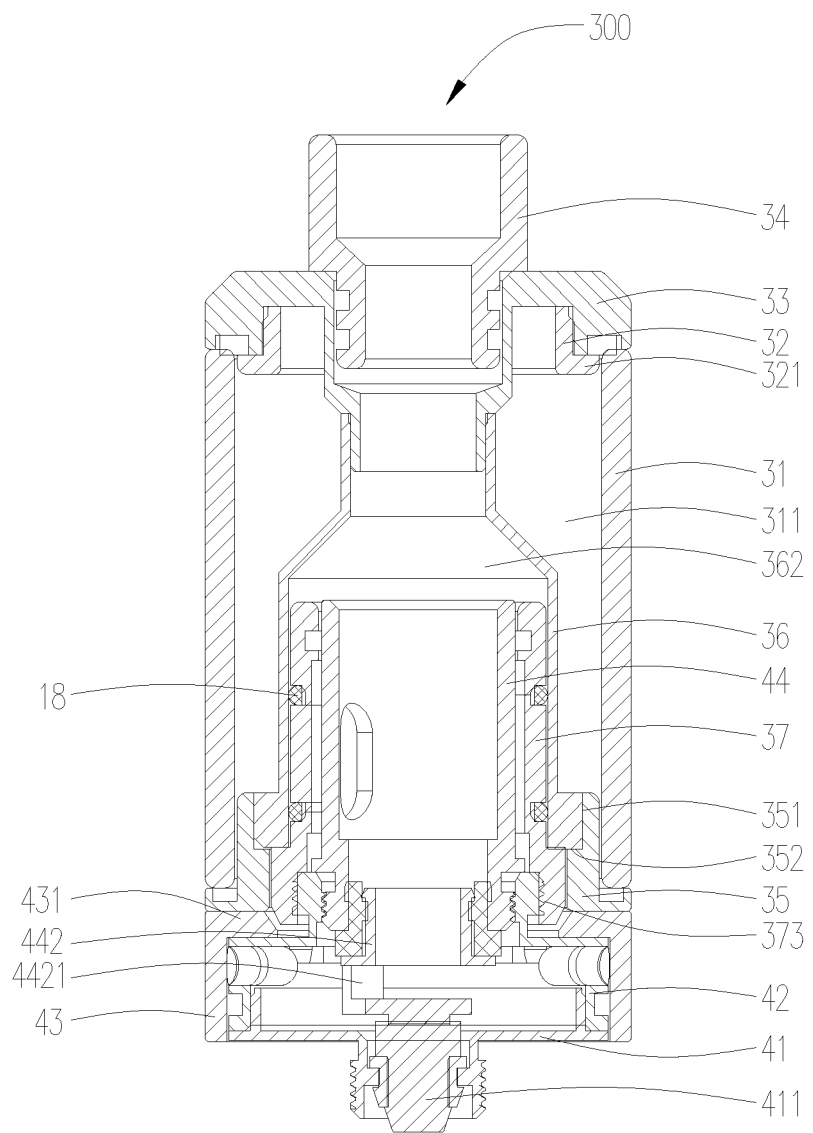
FIG. 18 is cross-sectional view of the electronic cigarette of FIG. 15 (showing a close state of the liquid storage chamber)

Also referring to FIG. 18, the lower cover 35 substantially has an annular structure, the circumferential surface of the lower cover 35 is fixedly connected to the internal circumferential surface of the liquid storage tube 31 by an interference fit. The internal wall of the upper end of the lower cover 35 defines an annular groove 351 arranged along a circumferential direction of the lower cover 35, the lower wall of the annular groove 351 forms a restriction portion 352.

The sealing member 36 substantially has a hollow tapered sleeve structure having two openings at opposite ends. The lower end of the sealing member 36 is provided with a pair of blocking portions 361 opposite to each other, the pair of blocking portion 361 extends downwardly from a lower end of the sealing member 36 along an axial direction of the sealing member 36. The upper end of the sealing member 36 is fixedly connected to the lower end of the upper cover 33. The lower end of the sealing member 36 is fixedly connected to the annular groove 351 via an interference fit, causing the blocking portion 361 of the sealing member 36 to resist the restricting portion 352.

Further, a liquid storage chamber 311 is constituted by an space between an internal wall of the liquid storage tube 31 and an external wall of the sealing member 36, the interior space of the sealing member 36 forms an exhaust passage 362. The sidewall of the sealing member 36 defines a second liquid intake hole 363 fluidly communicated with the liquid storage chamber 311.

The adjusting member 37 substantially has a hollow cylindrical structure, the adjusting member 37 is provided with an resisting portion 371. In the illustrated embodiment, the resisting portion 371 is a protrusion on a sidewall of the lower end of the adjusting member 37. The resisting portion 371 protrudes along an axial direction of the adjusting member 14 and can resist the restricting portion 352. During a rotation procedure of the adjusting member 37, the external circumferential surface of the adjusting closely contacts the internal circumferential surface of the sealing member 36 all the time.

Further, the sidewall of the adjusting member 37 defines a communicating portion 372 which can be fluidly communicated with the second liquid intake hole 363, the internal wall of the lower end of the adjusting member 37 defines internal threads 373.

In order to guarantee an air-tightness between the adjusting member 37 and the sealing member 36, and in order to strengthen a softness of rotating the adjusting member 37 at the same time, a first sealing member 38 is positioned between the adjusting member 37 and the sealing member 36. In the illustrated embodiment, the first sealing member 38 is positioned on the external wall of the adjusting member 37. It can be understood that, the first sealing member 38 can also be positioned on the internal wall of the sealing member 36.

It can be understood that, in alternative embodiment not shown, the connecting ring 32 can be omitted, at the time, the lower end of the upper cover 33 is directly fixedly connected to the upper end of the liquid storage tube 31.

The atomizing assembly 40 includes an atomizing base 41, an atomizing end cover 42 mounted on the atomizing base 41, an air regulating member 43 rotatably sleeved on the atomizing end cover 42, and an atomizing head 44 detachably connected to the upper end of the atomizing end cover 42.

The atomizing base 41 substantially has a round cup shape, a first electrode 411 is assembled to the center of the atomizing base 41 and is electrically connected to the battery pack. Further, the atomizing base 41 defines threads to engage the battery pack.

The atomizing end cover 42 substantially has an inverted round cup shape, the lower end of the atomizing end cover 42 is fixedly connected to the upper end of the atomizing base 41, the external wall of the upper end of the atomizing end cover 42 is provided with external threads 421 engaging the internal threads, the internal wall of the upper end of the atomizing end cover 42 is provided with first internal threads 422.

Further, the sidewall of the atomizing end cover 42 defines a first air intake hole (not labeled)

The air regulating member 43 substantially has an annular structure, the upper end of the air regulating member 43 forms a resisting portion 431 at an upper end, the resisting portion 431 extending inwardly from a circumferential surface of the air regulating member 43, the resisting portion 431 can engage the atomizing end cover 42 to prevent a detachment of the air regulating member 43.

Further, the sidewall of the air regulating member 43 defines a second air intake hole (not labeled) corresponding to the first air intake hole, the air regulating member 43 is rotated so as to enable the second air intake hole to fluidly communicating with the first air intake hole or enable the air regulating member 43 to seal the first air intake hole, thereby controlling the air inflow.

The atomizing head 44 is provided with first external threads 441 engaging with the first internal threads 422, a second electrode 442 is further assembled to the lower end of the atomizing head 44, the lower end of the second electrode 442 is electrically connected to the first electrode 411. The upper end of the second electrode 442 is electrically connected to the heating member (not shown) in the atomizing head 44, the heating member is heated to heat up the tobacco liquid flowing into the atomizing head 44 from the liquid storage chamber 311, causing the tobacco liquid to become aerosol for user to inhale.

Further, the second electrode 442 further defines a through hole 4421 fluidly communicated with the first air intake hole and the interior chamber of the atomizing head 44. At the time, the external air flow enters into the interior of the atomizing head 44 by passing through the second air intake hole, the first air intake, and the through hole 4421 successively, and is mixed with the aerosol, the mixed gas reaches user's mouth by passing through the exhaust passage 362, the upper cover 33 and the mouth piece 34 successively.

Further, an insulating member (not labeled) is positioned between the atomizing base 41 and the first electrode 411, and an insulating member (not labeled) is positioned between the atomizing head 44 and the second electrode 442, for provide an insulation function.

Figure 19:
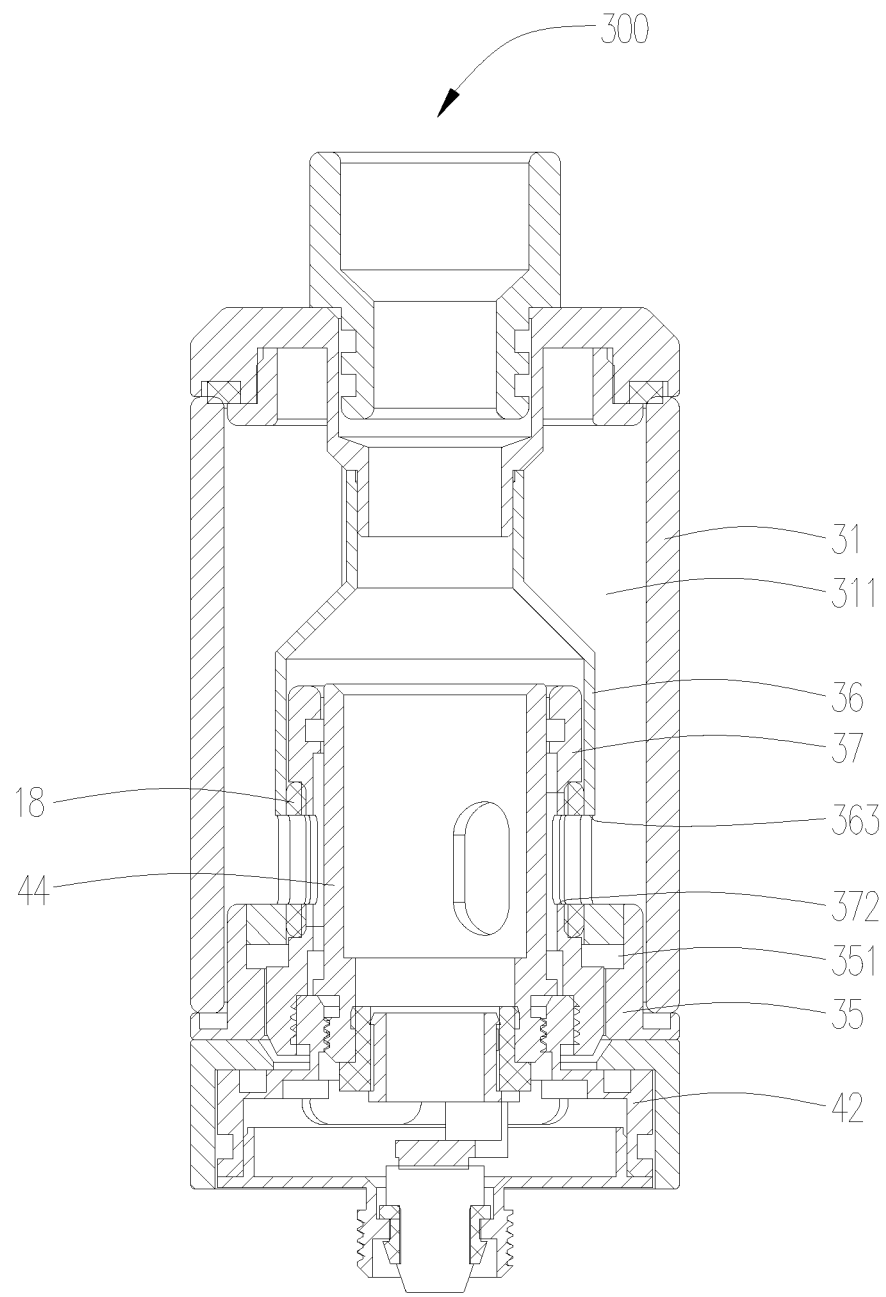
FIG. 19 is another cross-sectional view of the electronic cigarette of FIG. 15 (showing an open state of the liquid storage chamber)

The operation procedure of the electronic cigarette 300 of the present discourse is illustrated with reference to accompanying drawings as follow:

Referring to FIG. 19, when the liquid storage assembly 30 is connected and assembled to the atomizing assembly 40, firstly, the atomizing head 44 is connected to the atomizing end cover 42 via threads, and then the atomizing assembly 40 is rotated along a tightening direction, the adjusting member 37 gradually engages the atomizing end cover 42 by threads, when a screw force is greater than a friction force between the adjusting member 37 and the sealing member 36, the adjusting member 37 is then rotated together with the atomizing end cover 42. When the resisting portion 371 is rotated to reach and resist the blocking portion 361, the adjusting member 37 is then stopped. At the time, the second liquid intake hole 363 is fluidly communicated with the communicating portion 372, the liquid storage chamber 311 is opened. The tobacco liquid flows into the interior chamber of the atomizing head 44 by passing through the second liquid intake hole 363 and the communicating portion 372 successively, and is then atomized to generate aerosol. The atomizing assembly 40 is continually rotated to be tightened, until the atomizing end cover 42 and the adjusting member 37 is mounted on position.

Referring to FIG. 18, when the liquid storage assembly 30 is required to be disassembled and separated from the atomizing assembly 40, the atomizing assembly 40 is rotated along a loosened direction, at an initial time, the screw force is greater than a friction force between the adjusting member 37 and the sealing member 36. The adjusting member 37 is rotated together with the atomizing end cover 42, until the resisting portion 371 resists the other blocking portion 361, the adjusting member 37 is then stopped. At the time, the second liquid intake hole 363 is blocked from the communicating portion 372, the liquid storage chamber 311 is closed, and the tobacco liquid cannot flow out. The atomizing assembly 40 is continually rotated to be loosened, until the atomizing end cover 42 is separated from the adjusting member 37 completely.

Figure 20:
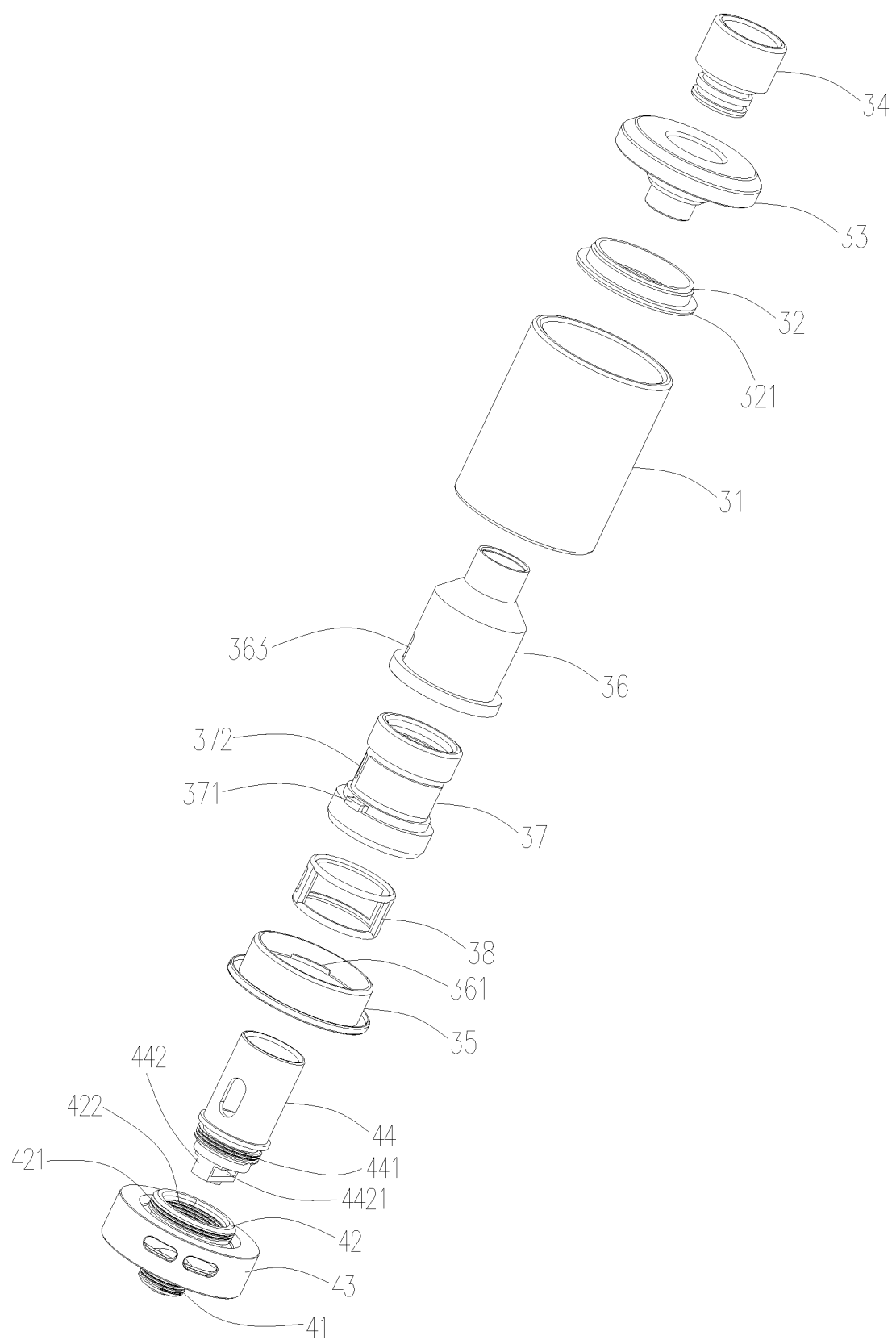
FIG. 20 is an exploded view of an electronic cigarette of a fourth embodiment of the present disclosure.

In the electronic cigarette 300 provided by the third embodiment of the present disclosure, when the liquid storage assembly 30 is detached and separated from the atomizing assembly 40, the adjusting member 37 is rotated to disconnect the communicating portion 372 from the second liquid intake hole 363, and the liquid storage chamber 311 is closed, the tobacco liquid cannot flow out. Even if it is opened by children, a leakage of the tobacco liquid cannot occur, a contact or swallowing of the tobacco liquid by children can be effectively avoided, it has a better safety performance The Fourth Embodiment Referring to FIG. 20, the difference between the electronic cigarette provided by the fourth embodiment of the present disclosure and the electronic cigarette 300 provided by the third embodiment is that, a number of the blocking portion 361 is two, the two blocking portions 361 are opposite to each other and are protruded from the restricting portion 352, when use, the resisting portion 371 can resist the restricting portion 352 along an axial direction and resist the blocking portion 361 along a circumferential direction, the specific operation procedure is same as that in the third embodiment, which is not specifically described herein.

In the electronic cigarette of the fourth embodiment, the blocking portion 361 is positioned on the lower cover 35, when the liquid storage assembly 30 is disassembled and separated from the atomizing assembly 40, a sealing function for the liquid storage chamber 311 can be provided, it has a better safety performance The embodiments described above are merely preferred embodiments, but not intended to limit the application. Any modifications, alternatives or improvements made within the principle and spirit of the present application should be interpreted as falling within the protection scope of the present application.

What is claimed is:

1. A liquid storage assembly, comprising:
a liquid storage tube having a liquid storage chamber;
a sealing member received in the liquid storage tube and defining a first liquid intake hole fluidly communicating with the liquid storage chamber;
an adjusting member received in the liquid storage tube and rotatable relative to the sealing member, the adjusting member defining a communicating portion corresponding to the first liquid intake hole; and
a lower cover positioned on an end of the liquid storage tube,
wherein the lower cover or the sealing member is provided with a blocking portion, the adjusting member is provided with a resisting portion capable of resisting the blocking portion, the adjusting member is rotatable to enable the resisting portion to reach and resist the blocking portion, causing the adjusting member to seal the first liquid intake hole to close the liquid storage chamber,
wherein an internal wall of the lower cover is provided with a restricting portion, a number of the blocking portion is two, the two blocking portions are opposite to each other and are protruded from the restricting portion, the resisting portion is capable of resisting the restricting portion along an axial direction and resisting the blocking portion along a circumferential direction.

2. An atomizer, comprising a liquid storage assembly according to claim 1, and an atomizing assembly detachably connected to the liquid storage assembly.

3. An electronic cigarette, comprising an atomizer according to claim 2, and a battery pack connected to the liquid storage assembly.

4. The liquid storage assembly according to claim 1, wherein the liquid storage tube is provided with an exhaust tube therein, the exhaust tube is arranged along an axial direction of the liquid storage tube and extends through the liquid storage tube, the liquid storage chamber is constituted by a space between an internal wall of the liquid storage tube and an external wall of the exhaust tube.

5. The liquid storage assembly according to claim 1, wherein the liquid storage assembly further comprises a pressing member received in the liquid storage tube, the pressing member defines a second liquid intake hole corresponding to the first liquid intake hole, the second liquid intake hole is fluidly communicating with the liquid storage chamber, the sealing member is provided with at least one positioning protrusion, the pressing member defines at least one positioning hole corresponding to the at least one positioning protrusion, the pressing member is fixedly connected to the sealing member via an engagement between the at least one positioning protrusion and the at least one positioning hole.

6. The liquid storage assembly according to claim 4, wherein the liquid storage assembly further comprises an auxiliary adjusting member fixed to the adjusting member and positioned between the adjusting member and the sealing member, the auxiliary adjusting member defines an auxiliary communicating portion corresponding to the communicating portion, an end of the auxiliary adjusting member away from the adjusting member rotatably resists the sealing member, the communicating portion is capable of fluidly communicating with the first liquid intake hole via the auxiliary communicating portion.

7. The liquid storage assembly according to claim 6, wherein the adjusting member is provided with at least one first protrusion, the auxiliary adjusting member defines at least one first latching groove corresponding to the at least one first protrusion, the adjusting member is fixedly connected to the auxiliary adjusting member via an engagement between the at least one first protrusion and the at least one first latching groove.

8. The liquid storage assembly according to claim 6, wherein the exhaust tube is provided with at least one protrusion at an end adjacent to the atomizing assembly, the at least one protrusion protrudes along an axial direction of the exhaust tube, the sealing member defines at least one latching groove corresponding to the at least one protrusion, the sealing member is fixedly connected to the liquid storage tube via an engagement between the at least one protrusion and the at least one latching groove.

9. The liquid storage assembly according to claim 6, wherein the sealing member and the auxiliary adjusting member are made of ceramic materials.

10. A liquid storage assembly, comprising:

a liquid storage tube having a liquid storage chamber;

a sealing member received in the liquid storage tube and defining a liquid intake hole fluidly communicating with the liquid storage chamber;

an adjusting member received in the liquid storage tube and rotatable relative to the sealing member, the adjusting member defining a communicating portion corresponding to the liquid intake hole; and a lower cover positioned on an end of the liquid storage tube, wherein the lower cover or the sealing member is provided with a blocking portion, the adjusting member is provided with a resisting portion capable of resisting the blocking portion, the adjusting member is rotatable to enable the resisting portion to reach and resist the blocking portion, causing the adjusting member to seal the liquid intake hole to close the liquid storage chamber, and wherein an internal wall of the lower cover is provided with a restricting portion, a number of the blocking portion is two, the two blocking portions are opposite to each other and are protruded along an axial direction of the sealing member from a lower end of the sealing member, the resisting portion is capable of resisting the restricting portion along the axial direction and resisting the blocking portion along a circumferential direction.

* * * * *